US007789913B2

(12) United States Patent
Collins et al.

(10) Patent No.: US 7,789,913 B2
(45) Date of Patent: Sep. 7, 2010

(54) METHODS FOR INJECTING A CURABLE BIOMATERIAL INTO AN INTERVERTEBRAL SPACE

(75) Inventors: Keith Collins, Milford, CT (US); Thomas G. Wilson, Guilford, CT (US); Jared Walkenhorst, Fairfield, CT (US); Dennis Lee, Milford, CT (US); Andrew Carter, Trumbull, CT (US); John Pafford, Eads, TN (US); Mark D. LoGuidice, Southport, CT (US); Lance Middleton, Soddy Daisy, TN (US); Lawrence Boyd, Durham, CT (US)

(73) Assignee: Spine Wave, Inc., Shelton, CT (US)

( * ) Notice: Subject to any disclaimer, the term of this patent is extended or adjusted under 35 U.S.C. 154(b) by 502 days.

(21) Appl. No.: 11/170,577

(22) Filed: Jun. 29, 2005

(65) Prior Publication Data

US 2006/0004458 A1    Jan. 5, 2006

Related U.S. Application Data

(60) Provisional application No. 60/583,665, filed on Jun. 29, 2004.

(51) Int. Cl.
*A61F 2/44* (2006.01)
(52) U.S. Cl. .................................................. 623/17.12
(58) Field of Classification Search ............. 606/90, 606/92–94, 192; 623/17.11–17.16
See application file for complete search history.

(56) References Cited

U.S. PATENT DOCUMENTS 4,313,434 A    2/1982 Segal (Continued)

FOREIGN PATENT DOCUMENTS

EP    0 277 282    8/1991

(Continued)

OTHER PUBLICATIONS

Premarket Notification [510(k)] Summary, "Kyphx Directional Inflatable Bone Tamps", Kyphx Directional Inflatable Bone Tamp-Traditional 510(k), Kyphon Inc., Sep. 15, 2003, 5 pages).

(Continued)

*Primary Examiner*—Thomas C Barrett
*Assistant Examiner*—Michael J Araj
(74) *Attorney, Agent, or Firm*—Maginot, Moore & Beck, LLP

(57) ABSTRACT

A method for treating a diseased or damaged spinal disc comprises the steps of: (a) providing access to the nucleus pulposus through the annulus; (b) removing at least a portion of the nucleus pulposus to create an intradiscal space; determining the size of the intradiscal space; and (c) sealably introducing under pressure a curable biomaterial through the annulus directly into the intradiscal space. The method may include the additional steps of applying a force to distract the opposing vertebral bodies about the intradiscal space and then removing the distraction force after the biomaterial has cured. The step of determining the size of the intradiscal space may be accomplished by expanding a compliant balloon within the intradiscal space using a contrast medium capable of visualization under fluoroscopy. The curable material is sealably introduced through a vented needle inserted through the opening. The curable biomaterial is introduced until a quantity of the material flows into the vent.

66 Claims, 9 Drawing Sheets

U.S. PATENT DOCUMENTS

| | | | |
|---|---|---|---|
| 4,492,576 A | | 1/1985 | Dragan |
| 4,684,363 A | | 8/1987 | Ari et al. |
| 4,772,287 A | | 9/1988 | Ray et al. |
| 4,793,351 A | | 12/1988 | Landman et al. |
| 4,969,888 A | * | 11/1990 | Scholten et al. ............... 606/94 |
| 5,108,404 A | | 4/1992 | Scholten et al. |
| 5,300,035 A | | 4/1994 | Clement |
| 5,331,975 A | | 7/1994 | Bonutti |
| 5,344,439 A | | 9/1994 | Otten |
| 5,411,491 A | * | 5/1995 | Goldhardt et al. ........... 604/247 |
| 5,454,365 A | | 10/1995 | Bonutti |
| 5,514,153 A | | 5/1996 | Bonutti |
| 5,549,565 A | | 8/1996 | Ryan et al. |
| 5,562,736 A | | 10/1996 | Ray et al. |
| 5,667,520 A | | 9/1997 | Bonutti |
| 5,685,826 A | | 11/1997 | Bonutti |
| 5,720,726 A | | 2/1998 | Marcadis et al. |
| 5,752,969 A | | 5/1998 | Cunci et al. |
| 5,762,629 A | | 6/1998 | Kambin |
| 5,817,303 A | | 10/1998 | Bonutti |
| 5,827,318 A | | 10/1998 | Bonutti |
| 5,860,997 A | | 1/1999 | Bonutti |
| 5,888,220 A | | 3/1999 | Felt et al. |
| 5,954,739 A | | 9/1999 | Bonutti |
| 5,968,062 A | | 10/1999 | Thomas et al. |
| 6,017,305 A | | 1/2000 | Bonutti |
| 6,033,654 A | | 3/2000 | Stedronsky et al. |
| 6,039,761 A | | 3/2000 | Li et al. |
| 6,042,596 A | | 3/2000 | Bonutti |
| 6,083,202 A | | 7/2000 | Smith |
| 6,135,999 A | | 10/2000 | Fanton et al. |
| 6,174,311 B1 | | 1/2001 | Branch et al. |
| 6,187,023 B1 | | 2/2001 | Milner et al. |
| 6,187,048 B1 | | 2/2001 | Milner et al. |
| 6,210,397 B1 | | 4/2001 | Aboul-Hosn et al. |
| 6,224,630 B1 | | 5/2001 | Bao et al. |
| 6,245,107 B1 | | 6/2001 | Ferree |
| 6,248,131 B1 | | 6/2001 | Felt et al. |
| 6,264,659 B1 | | 7/2001 | Ross et al. |
| 6,306,177 B1 | | 10/2001 | Felt et al. |
| 6,370,420 B1 | | 4/2002 | Kraft |
| 6,371,990 B1 | | 4/2002 | Ferree |
| 6,402,784 B1 | | 6/2002 | Wardlaw |
| 6,423,333 B1 | | 7/2002 | Stedronsky et al. |
| 6,436,143 B1 | | 8/2002 | Ross et al. |
| 6,443,998 B1 | | 9/2002 | Felt et al. |
| 6,468,527 B2 | | 10/2002 | Austin et al. |
| 6,558,390 B2 | | 5/2003 | Cragg |
| 6,579,291 B1 | | 6/2003 | Keith et al. |
| 6,726,691 B2 | * | 4/2004 | Osorio et al. ................. 606/94 |
| 6,805,695 B2 | | 10/2004 | Keith et al. |
| 6,921,532 B1 | | 7/2005 | Austin et al. |
| 6,981,981 B2 | | 1/2006 | Reiley et al. |
| 7,004,945 B2 | * | 2/2006 | Boyd et al. ................... 606/92 |
| 7,229,633 B2 | | 6/2007 | Austin et al. |
| 7,235,255 B2 | | 6/2007 | Austin et al. |
| 2002/0045942 A1 | | 4/2002 | Ham |
| 2002/0147497 A1 | | 10/2002 | Belef et al. |
| 2003/0009227 A1 | | 1/2003 | Lambrecht et al. |
| 2003/0033017 A1 | | 2/2003 | Lotz et al. |
| 2003/0082169 A1 | | 5/2003 | Boyd |
| 2003/0083641 A1 | | 5/2003 | Angel et al. |
| 2003/0083642 A1 | * | 5/2003 | Boyd et al. ................. 604/506 |
| 2004/0059339 A1 | | 3/2004 | Roehm, III et al. |
| 2004/0073213 A1 | | 4/2004 | Serhan et al. |
| 2004/0098017 A1 | | 5/2004 | Saab et al. |
| 2004/0186471 A1 | | 9/2004 | Trieu |
| 2004/0229878 A1 | | 11/2004 | DiMauro et al. |
| 2005/0070913 A1 | | 3/2005 | Milbocker et al. |
| 2005/0095235 A1 | | 5/2005 | Austin et al. |
| 2005/0102030 A1 | | 5/2005 | Yuksel et al. |
| 2005/0209555 A1 | | 9/2005 | Middleton et al. |
| 2005/0209601 A1 | | 9/2005 | Bowman et al. |
| 2005/0209602 A1 | | 9/2005 | Bowman et al. |
| 2005/0234425 A1 | | 10/2005 | Miller et al. |
| 2006/0253200 A1 | * | 11/2006 | Bao et al. ................. 623/17.12 |

FOREIGN PATENT DOCUMENTS

FR             2 639 823         12/1988

OTHER PUBLICATIONS

510(k) Summary of Safety and Effectiveness, "KyphX™ Inflatable Bone Tamp", Feb. 14, 2001, 5 pages.

Boyd, Lawrence M., Mahar, Andrew and Capello, Joseph, "Injectable Biomaterials for Augmentation of the Nucleus Pulposus", International Symposium-Non-Fusion Techniques in Spinal Surgery, Feb. 14, 2003, 12 pages.

Mahar et al., "Biomechanical Efficacy of a Protein Polymer Hydrogel for Inter-Vertebral Nucleus Augmentation and Replacement", World Congress of Biomechanics, Calgay, Canada, Aug. 5, 2002, 4 pages.

Kitchel, Scott and Cappello, Joseph, "Injectable Biomaterials for Augmentation of the Nucleus Pulposus", http://127.0.0.1:8080/SAC3C1/presentation_list8.php, Apr. 25, 2005, 6 pages.

Garfin, Steven R. Yuan, Hansen A., and Reiley, Mark A., "Kyphoplasty and Vertebroplasty for the Treatment of Painful Osteoporatic Compression Fractures", SPINE, vol. 2, No. 14, pp. 1511-1515, 2001 © Lippincott Williams & Wilkins, Inc. 5 pages.

Lieberman et al., "Initial Outcome and Efficacy of "Kyphoplasty" in the Treatment of Painful Osteoporatic Vertebral Compression Fractures", SPINE, vol. 26, No. 14, pp. 1631-1638, 8 pages.

Disc Dynamics, "DASCOR Disc Arthroplasty System", web page excerpt. Published Feb. 2004. Particular attention is directed to Step Three of the described procedure.

* cited by examiner

METHODS FOR INJECTING A CURABLE BIOMATERIAL INTO AN INTERVERTEBRAL SPACE

REFERENCE TO RELATED APPLICATION

The present application claims priority to co-pending provisional application No. 60/583,665, entitled "SYSTEMS AND METHODS FOR INJECTING A CURABLE BIOMATERIAL INTO AN INTERVERTEBRAL SPACE", filed on Jun. 29, 2004, the entire disclosure of which is incorporated herein by reference.

BACKGROUND OF THE INVENTION

The present invention relates to systems and methods for the treatment of the spine, and especially the interbody disc space. More specifically, the invention concerns the injection of a biomaterial into a spinal space, such as the intradiscal space.

Spine fusion procedures represent the state of the art treatment for intervertebral disc problems, which generally involve open surgery and the use of interbody fusion cages and spinal fixation systems to stabilize the fusion site. An alternative treatment under evaluation is to replace the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices use a deflated balloon attached to a cannula and inserted between the vertebral bodies. The balloon is inflated with a prosthetic fluid through the cannula to distract the vertebral bodies. This requires high-pressure delivery of the fluid to achieve the pressure needed to distract the vertebral bodies and the balloon and fluid permanently remain in the disc space. Alternatively, a separate device is used to inject the prosthetic fluid around the balloon and the balloon is used strictly for distraction after which it is deflated and removed.

U.S. Pat. No. 4,772,287 ("Ray I") discloses a bladder injected with thixotropic gel implanted between two vertebral bodies to restore the disc height. The technique described requires that the vertebral bodies are first distracted and a bore drilled to allow for insertion of the bladder.

U.S. Pat. No. 5,562,736 ("Ray II") discloses a method for implanting a prosthetic disc nucleus. Ray II discloses cutting a first and second flap in the annulus. The flaps provide access to the nucleus. Ray II then discloses using an inflatable jack to distract the disc space prior to insertion of the prosthetic spinal disc nucleus. The jack has a deflated balloon on its end that is inserted into the nucleus through one of the flaps. The balloon is inflated with fluid causing the vertebral bodies to distract. Once the vertebral bodies are sufficiently distracted the fluid flow is stopped and the prosthetic spinal disc nucleus is inserted through the other flap. The balloon is then deflated and the second prosthetic spinal disc nucleus is inserted. The flaps are closed and placed in contact with the annulus by a suture, staple or glue.

U.S. Pat. No. 6,187,048 ("Milner") discloses an implant for an intervertebral disc nucleus pulposus prosthesis made from a conformable, in-situ curable, material which is resiliently deformable. Milner discloses removing the nucleus material, then either injecting through the annulus or creating an opening in the annulus to deliver a curable material under pressure into the nucleus space. The pressure is necessary to ensure conformation to the nucleus space and/or to increase the internal pressure of the disc space to distract the vertebral bodies. The amount of pressure needed to distract the disc space is high and may allow the material to flow through cracks or voids in the annulus into the disc space. Milner also describes an embodiment where the curable material is injected into a flexible container that is inserted first into the nucleus space in a deflated state and inflated by the material as the material is injected. This method relies on the pressure of the fluid as it is injected to distract the vertebral bodies. Although this avoids the problem of the material leaking through the annulus, it imposes certain constraints such as a designing a cover of the correct shape and size suitable for safe injection of the curable material and prevention of leakage of the material from the cover once filled.

U.S. Pat. No. 6,248,131 ("Felt") describes distracting and injecting at the same time using a balloon device. The balloon can be used as a shell for containing the injected curable biomaterial and also used as a distraction means as the material is injected. Another embodiment describes the balloon as a cylinder shape which when inflated inside the disc space bears against the endplates for the vertebral bodies and distracts them. Then a second device is used to inject the curable biomaterial around the balloon cylinder. The material is allowed to cure and then the balloon is removed and a second curable biomaterial can be injected into the space left where the balloon was. In sum, when Felt discloses injecting material outside of the balloon, Felt discloses using a second device to carry out the injection. Insertion of this second device into the disc should typically require a second breach of the annulus fibrosis.

Much of the prior art contemplates free injection of biomaterial into a spinal space which may lead to uncontrolled leakage. The art also describes injection of the material into a deflated balloon, which requires leaving the balloon inside the disc space. Lastly, some methods require insertion under high pressure, thereby creating a potential for the prosthetic fluid to ooze or seep out of the disc space intra-operatively.

There is therefore a need for a system and method for introducing a biomaterial into a spinal space that is not prone to the problems of the prior art, especially the leakage problem experienced by the high pressure injection systems. This need extends to systems that can be easily utilized in a minimally invasive procedure.

SUMMARY OF THE INVENTION

This need is address by the methods of the present invention for treating a diseased or damaged spinal disc having an inner nucleus pulposus and an outer annulus. One method comprises the steps of: (a) providing access to the nucleus pulposus through the annulus; (b) removing at least a portion of the nucleus pulposus to create an intradiscal space; determining the size of the intradiscal space; and (c) sealably introducing under pressure a curable biomaterial through the annulus directly into the intradiscal space. The access may be provided by an extraforaminal approach to the disc, particularly an approach selected from the group of surgical entries consisting of a lateral retroperitoneal approach and a paramedian approach through the paraspinal muscles. The access may be an opening extending through the annulus that is formed by an annulotomy. In certain embodiments, the annulotomy creates a cruciate form.

In accordance with one aspect of the inventive method, the step of determining the size of the intradiscal space is practiced by expanding an inflatable device within the intradiscal space. The inflatable device may be a compliant balloon inserted into the intradiscal space in a deflated condition and inflated within the intradiscal space until it stops against the far border of the intradiscal space. In certain embodiments, the balloon is filled with a contrast medium capable of visualization under fluoroscopy.

In certain steps of the method, the curable material is sealably introduced through a needle inserted through the opening. This introduction may further include the step of providing a vent in communication with the intradiscal space, with the needle and the vent inserted through the opening. According to one aspect, the curable biomaterial is introduced until a quantity of the material flows into the vent.

The method may further include the step of providing a seal for sealing the annulus opening. This step may be accomplished by a seal is provided on the needle. The seal may comprise a compressible portion, so that the method contemplates the further step of placing the compressible portion against the exterior surface of the annulus adjacent to the opening. The seal may be configured to have a boss portion projecting from the compressible portion and configured to reside in the opening of the annulus. According to certain embodiments, the compressible portion is pressed by manual pressure against the exterior surface of the annulus and is held against the exterior surface for a period of time to allow at least a partial curing of the biomaterial.

The present invention contemplates injection of the biomaterial under pressure. In a specific embodiment, the curable biomaterial is injected into the intradiscal space through the needle under relatively low pressure. The injection pressure may be less than about 100 psi, or in a specific embodiment within the range of about 25 to 40 psi. For the low pressure injection, the pressure may be applied manually with a syringe.

In a further step within the scope of the present invention, a force is applied to distract the opposing vertebral bodies about the intradiscal space. The distraction force may be removed prior to the step of introducing the biomaterial into the intradiscal space. In this respect, the invention further contemplates a method of treating a diseased or damaged spinal disc between opposing vertebral bodies having an inner nucleus pulposus and an outer annulus, comprising the steps of: (a) forming an opening through the annulus to provide access to the nucleus pulposus; (b) removing at least a portion of the nucleus pulposus to create an intradiscal space; (c) applying a force to distract the opposing vertebral bodies about the intradiscal space; (d) removing the distraction force; and then (e) sealably introducing under pressure a curable biomaterial through the opening directly into the intradiscal space.

According to certain embodiments, the distraction force may be applied by inserting an inflatable device through the opening in a deflated condition and inflating the inflatable device within the intradiscal space. The inflatable device may be a non-compliant balloon that is configured to provide a limit to lateral expansion upon inflation but to allow further expansion in the direction of the opposing vertebral bodies. In these embodiments, the distraction force may be held for a period of time sufficient to allow the distracted vertebral bodies to remain substantially distracted by natural stretching of ligaments surrounding the vertebral bodies.

Certain methods contemplate that the distraction force is applied by inflating the balloon to a first pressure and held at the pressure for the period of time. This first pressure is up to about 200 psi and is released after a pre-determined period of time, after which the balloon may be removed from the intradiscal space.

According to some embodiments, the biomaterial is sealably introduced into the intradiscal space by injection through a needle inserted through the opening. With this approach, the biomaterial is preferably injected into the intradiscal space at a second pressure lower than the first pressure. This second pressure is less than about 100 psi, and preferably within the range of about 25-40 psi. A vent may be provided in communication with the intradiscal space to exhaust the intradiscal space and allow biomaterial to seep out when the intradiscal space is substantially filled.

It is one object to provide a method to facilitate introduction of a curable biomaterial into an intervertebral disc. One benefit achieved by the present invention is the ability to introduce the biomaterial under pressure and to the extent necessary to treat the affected disc. Other benefits and objects of the invention will become apparent upon consideration of the following written description, taken together with the accompanying figures.

DESCRIPTION OF THE PREFERRED EMBODIMENTS

Figure 1:
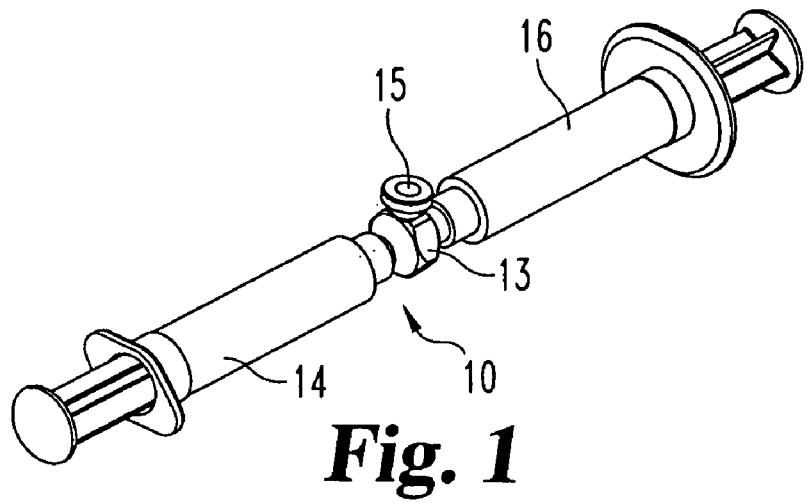
FIG. 1 is a perspective view of a mixing system for mixing an injectable biomaterial.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In one embodiment of the invention, adjacent vertebral bodies are distracted (by a non compliant balloon) at a predetermined pressure, such as at 200 psi (13 atmospheres). Using a non compliant balloon ensures that there is no lateral loading, or pressurization of the annulus, thereby avoiding the risk of damaging the annulus. The balloon (and thereby the distraction device) is then removed allowing the distracted vertebral bodies to remain distracted due to the natural stretching of the surrounding ligaments. The distraction with the balloon under pressure is held for a period of time sufficient to stretch the ligaments and to cause the distraction to be maintained even after the balloon is removed. This period of time will vary between patients; however, it in certain procedures a period of about 20-30 seconds has been sufficient. While there may be some slight contraction of the ligaments initially, the vertebral bodies will remain spaced apart at a substantially desired spacing for some time to then enable introduction of biomaterial into the distracted disc space.

The biomaterial is sealably introduced under pressure that is not as high as used for the distraction step but that is sufficient so that the biomaterial will completely fill the space (or the partial space in a partial discectomy). Moreover, the injection pressure for the biomaterial is sufficient to recover any small amount of contraction that may occur when the balloon is removed. In accordance with one feature of the invention, the injection of the biomaterial occurs under low pressure. This pressure is nominally less than 100 psi, and in specific embodiments is in the range of 25-40 psi. A vent is used to exhaust the disc space and allow body fluid and/or air as well as biomaterial to seep out when the space is filled. Seepage of biomaterial indicates a complete fill of the disc space.

The low pressure on the biomaterial is held until the biomaterial is cured. This cure time is material dependent, but often falls in the range of about 5 minutes. Maintaining the pressure until curing also maintains the distracted disc space under hydrostatic pressure. Even under the low pressure, a seal must be provided around the opening in the annulus through which biomaterial is introduced. The seal in one arrangement is disposed on the material injection tube and is applied against the exterior surface of the annulus adjacent the opening.

In one embodiment of the invention, a surgical technique is provided for the use of injectable disc nucleus (IDN) as a replacement for the natural nucleus pulposus. The IDN is preferably a curable biocompatible polymer with properties that emulate those of the natural human disc. A suitable IDN material is disclosed in U.S. Pat. Nos. 6,423,333; 6,033,654; and 5,817,033, which issued to Protein Polymer Technologies, Inc. The disclosures or these patents are incorporated herein by reference. These patents disclose a proteinaceous curable polymer that has physical properties close to those of the human disc and that includes certain adhesive properties that allow the polymer to adhere to the disc annulus and any remaining disc nucleus pulposus.

Figure 2:
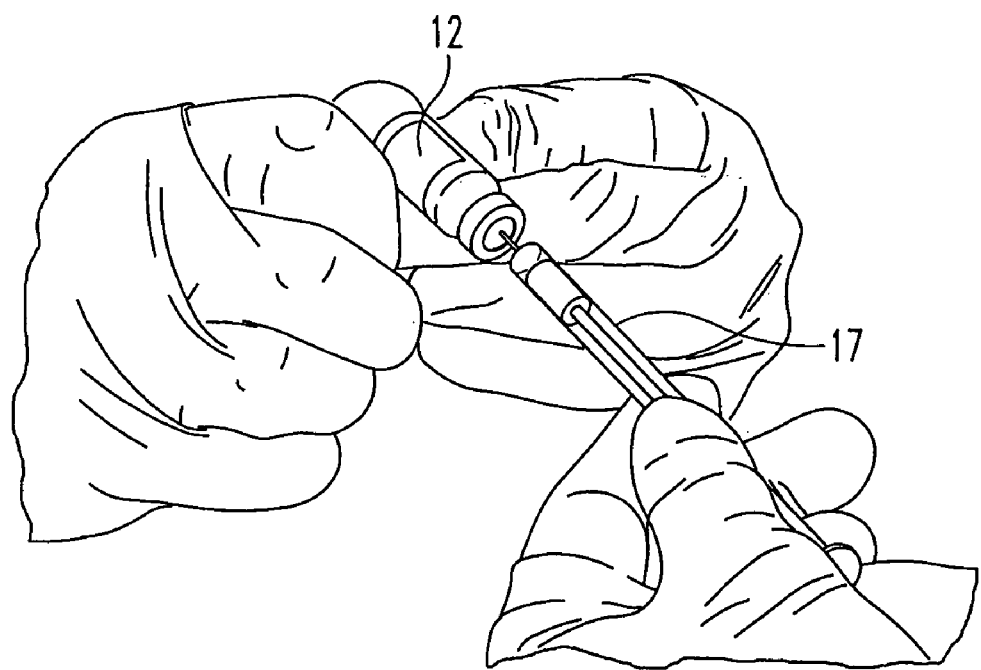
FIG. 2 is a pictorial view of the withdrawal of a cross-linker to be added to the biomaterial in the mixing system shown in FIG. 1.
Figure 3:
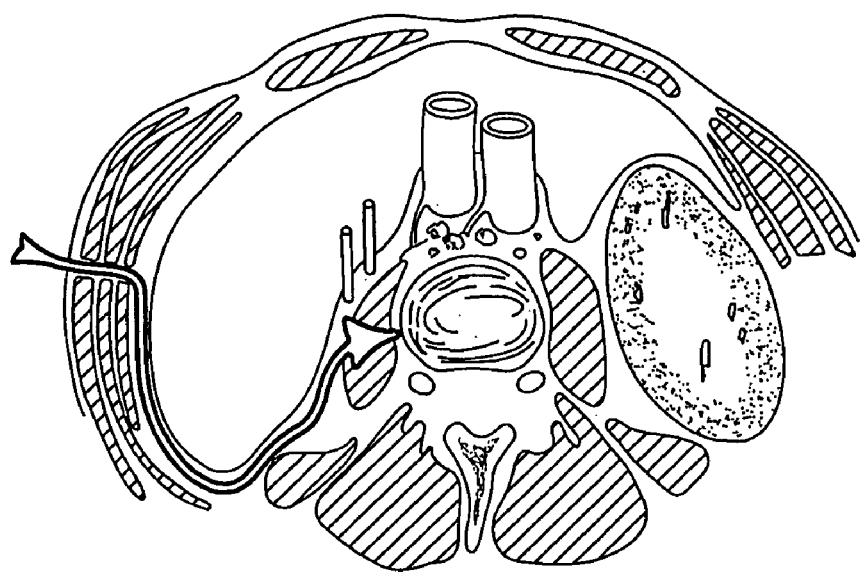
FIGS. 3-5 are diagrammatic view of surgical approaches to the intervertebral disc.
Figure 4:
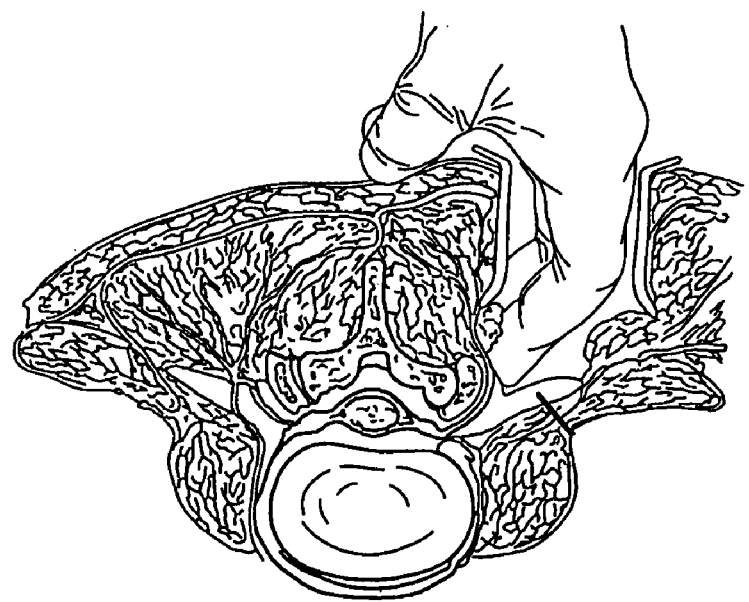
Figure 5:
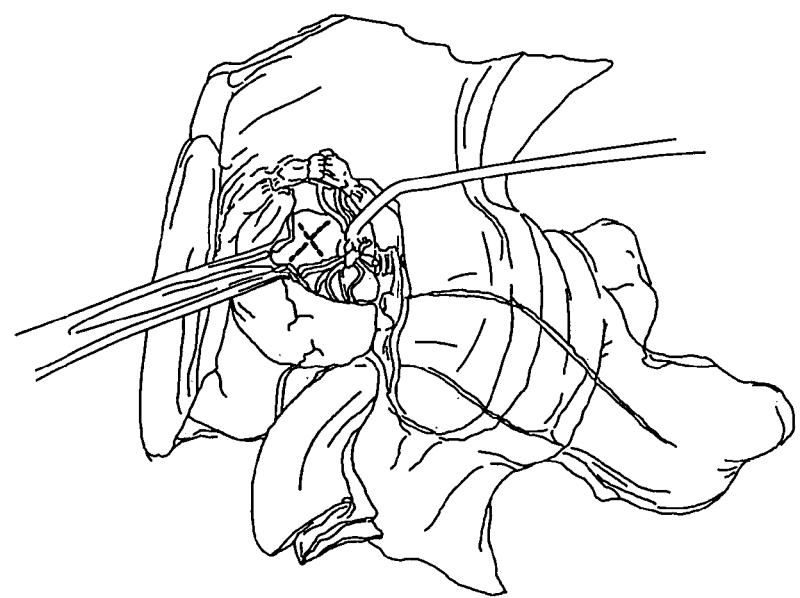

In a first step of the technique, a mixing system 10 is provided for mixing the constituents of the IDN material, as shown in FIG. 1. The mixing system 10 may be constructed as disclosed in co-pending application Ser. No. 10/803,214, entitled "Systems and Methods for Mixing Fluids". The entire disclosure of this application is incorporated herein by references, and particularly the discussion of the embodiment shown in FIGS. 3-9 in that application. In a specific embodiment, the mixing system 10 is prepared prior to the start of surgery by loading the assembly with four mL of a polymer constituent. This volume is mixed with a cross-linker constituent. In the specific embodiment, the volume is mixed with 34±1 μL of crosslinker drawn from a sterile vial 12 into a 100 μL syringe 14, purged of air, as shown in FIG. 2. The syringe is placed on the sterile table until it is needed for the mixing and injection step.

Where the biomaterial is an IDN, access to the intradiscal space is required. While many surgical approaches may be used, in one specific embodiment, the surgeon will use an extraforaminal mini-open approach to the disc. This may be either by a lateral retroperitoneal approach (FIG. 3) or a paramedian approach (FIG. 4) through the paraspinal muscles of the back. Access to the nucleus is gained through an extraforaminal annulotomy, so as to not expose the spinal canal or foramen to any undue risk. The annulus is identified and a minimal annulotomy is performed to gain access to the intradiscal space. If necessary, a cruciate annulotomy of up to 5 mm×5 mm may be used. The annulotomy should be oriented obliquely with one cut oriented with the outer fibers of the annulus, as shown in FIG. 5. The nucleus pulposus is then partially or completely removed using known techniques, such as using pituitary rongeurs and/or curettes. Alternatively, a mechanical method such as endoscopic shaving, hydraulic or radiofrequency (RF) technology may be used. The nucleotomy should be fully irrigated once all loose fragments have been manually removed.

Figure 6:
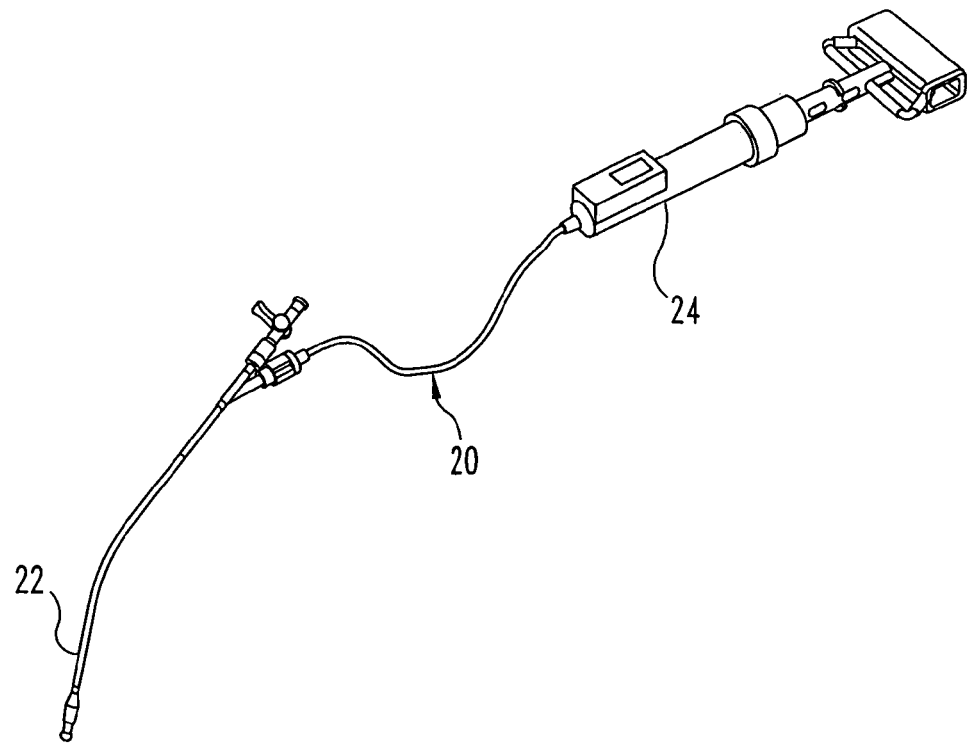
FIG. 6 is a pictorial view of a trial balloon assembly for use in a method of one embodiment of the present invention.
Figure 7:
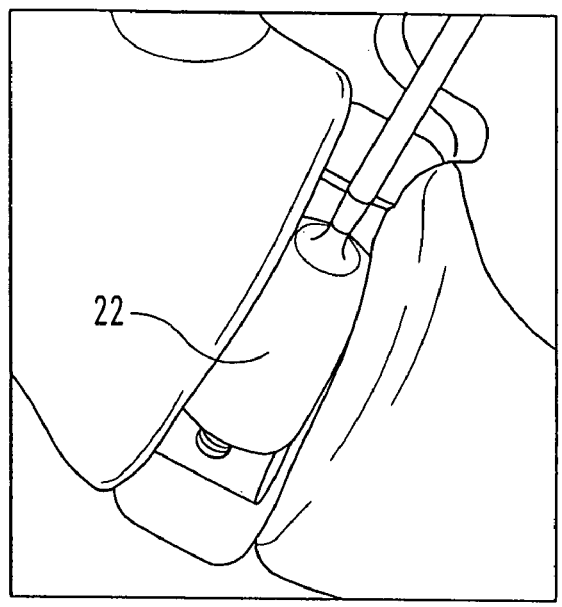
FIG. 7 is a pictorial representation of the use of the trial balloon shown in FIG. 6 in accordance with one aspect of the invention.
Figure 17:
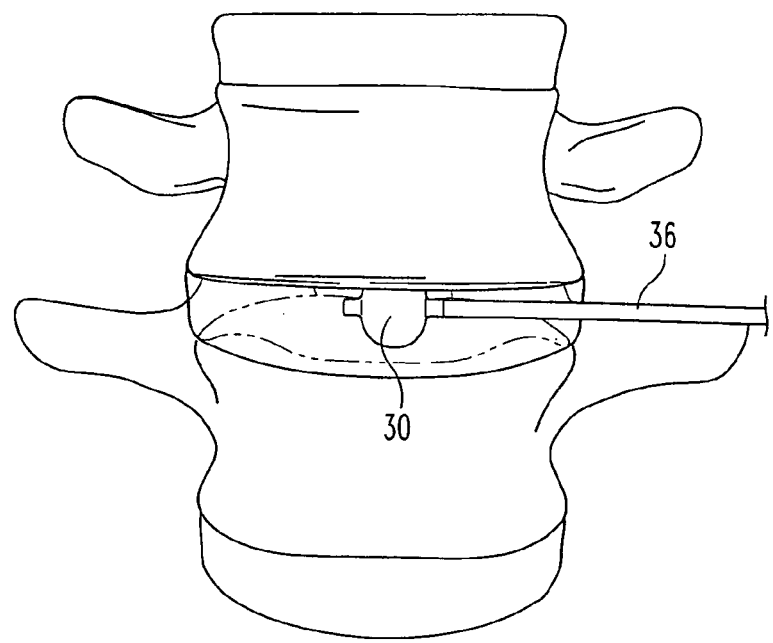
FIG. 17 is an enlarged pictorial view of the distraction balloon shown in FIG. 9.

The prepared nuclear cavity should be visualized prior to proceeding using a compliant trial balloon assembly 20, as depicted in FIG. 6. Once the balloon 22 is assembled to the inflation syringe 24 and primed with an inflation medium, the balloon is inserted through the annulotomy until it stops against the far border of the nucleotomy space. Preferably, the inflation medium is a fluid contrast medium that can be visualized under fluoroscopy. Injection of contrast media into the balloon and inflation under light pressure will allow the surgeon to judge the location and size of the space (FIGS. 7 and 17). In certain embodiments, the disc space can be visualized and the inflated size of the trial balloon measured to determine the distracted size of the disc space. An endoscopic camera may also be used to inspect the interior of the nucleotomy space, if desired by the surgeon.

If further removal of nucleus pulposus is indicated, the balloon can be removed and the nucleotomy continued. This iterative process may be repeated until the surgeon is satisfied with the size and location of the nucleotomy. In one feature of the invention, the final volume of contrast media injected into the balloon may then be used to estimate the volume of the nucleotomy and determine the amount of IDN that will be needed to fill the space.

Figure 8:
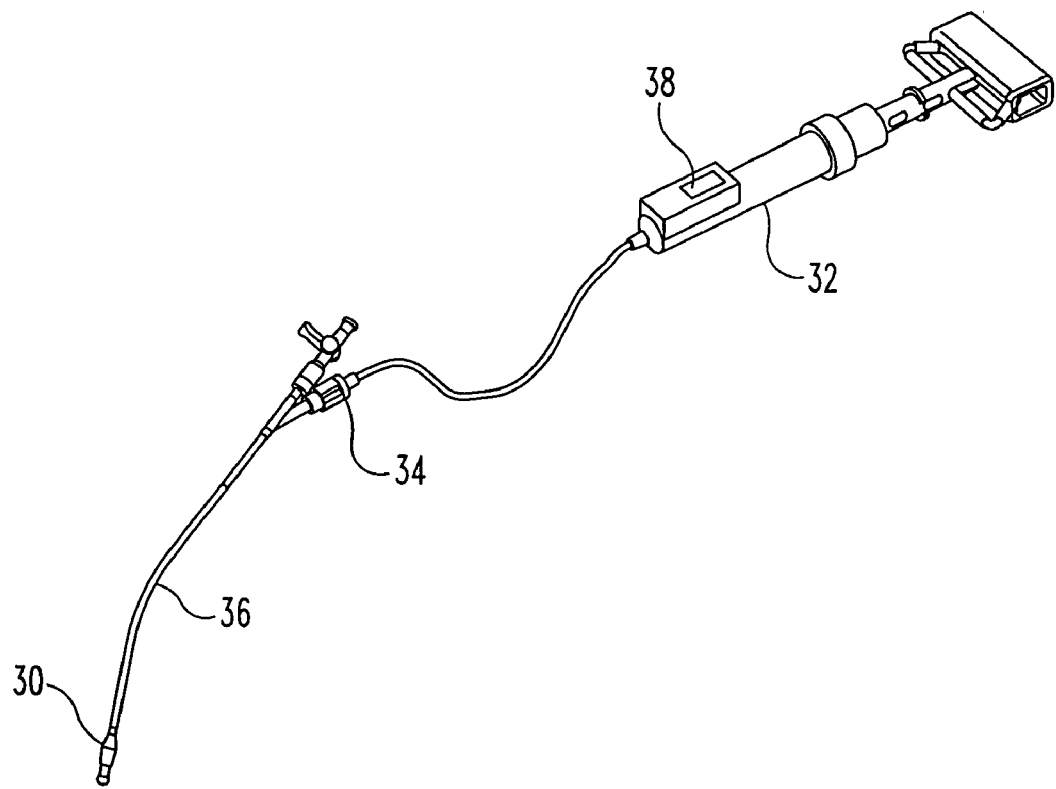
FIG. 8 is a pictorial view of a distraction balloon for use in a further aspect of the present invention.

Once the size of the space has been determined, the next step of the present invention involves distracting the space. In one embodiment, distraction of the disc is accomplished using a spherical balloon 30, such as a 15 mm diameter spherical balloon. The balloon is made of a non-compliant material and is adapted to provide a distraction force against the endplates of the disc. In a specific embodiment, the balloon 30 is able to be pressurized to approximately 13 atmospheres (200 psi). It is inflated using an inflation syringe 32 attached to the Luer fitting 34 on the catheter 36 of the balloon, as shown in FIG. 8. Pressure feedback is preferably obtained through tactile feel in the inflation syringe and a pressure gage 38 mounted on the body of the inflation syringe.

Figure 9:
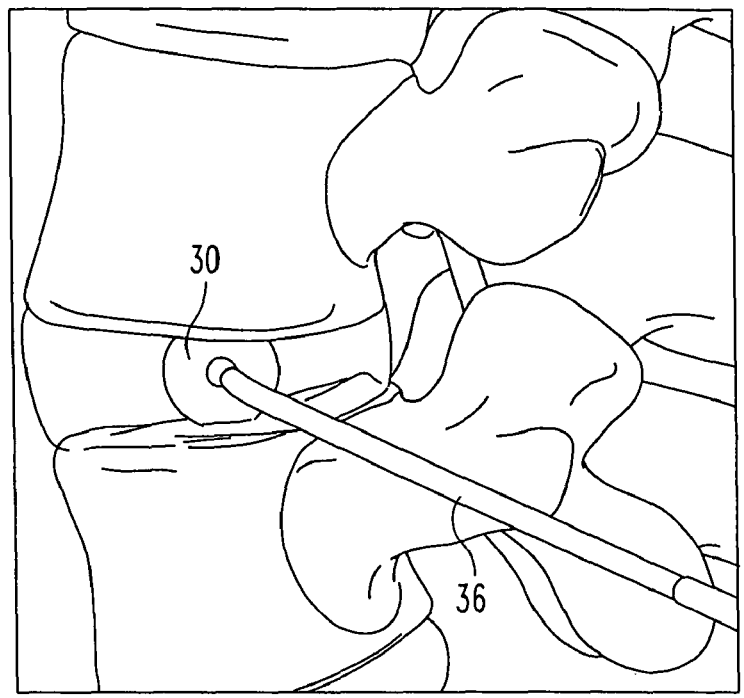
FIG. 9 is a pictorial representation of the distraction balloon of FIG. 8 shown in situ.
Figure 10:
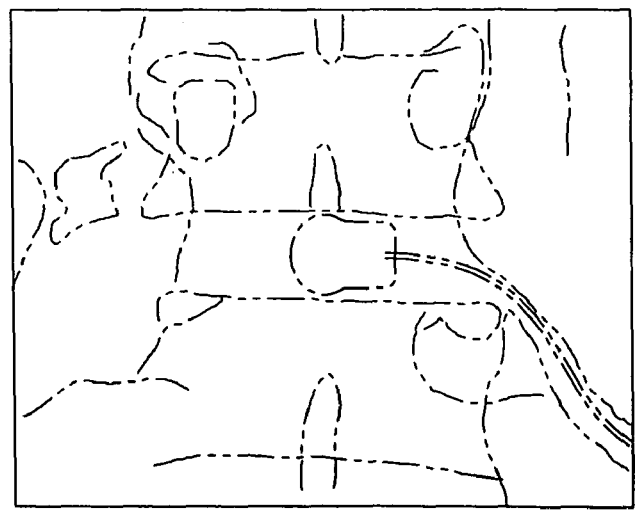
FIG. 10 is a fluoroscopic view of a distraction balloon in situ.

Once the syringe and balloon are primed with contrast media, the balloon is inserted into the disc space until it stops against the far border of the nucleotomy, as shown in FIG. 9. The balloon is gradually inflated until it contacts the endplates and ultimately pushes apart the endplates to achieve the desired amount of distraction (FIG. 10). Care should be taken to ensure the pressure rating of the balloon is not exceeded and that the endplates are not compromised by over-distraction.

Once the desired amount of distraction has been obtained, the balloon is deflated and removed from the disc. At this point, the trial balloon 22 may be used again to evaluate the resulting final nucleotomy. If the trial balloon is re-used, the resulting fluid volume may again be used to estimate the volume of IDN needed to the fill the distracted space.

Alternatively, distraction may be obtained using the surgeon's preferred technique. Other distraction techniques such as laminar distraction, screw/pin distraction, patient positioning, and traction may be used. As preservation of an intact endplate is important, the distraction technique may need to be altered from patient to patient in order to address this matter. One technique may be preferred over others in certain instances due to patient bone quality and anatomy. If additional distraction is applied, the trial balloon 22 may be used again to provide an estimate of the requisite IDN fluid volume.

In one feature of the invention, the distraction of the disc space is maintained by the patient's anatomy, rather than by a distraction device maintained in the disc space. It has been found that if the distraction accomplished as described above is maintained for a certain length of time the spinal ligaments will stretch and retain their lengthened configuration for sufficient time to inject the IDN and allow it to cure. In a specific embodiment, maintaining the distraction for about five minutes was sufficient to cause the surrounding ligaments to maintain the distraction long enough to complete the IDN injection and curing process.

Figure 11:
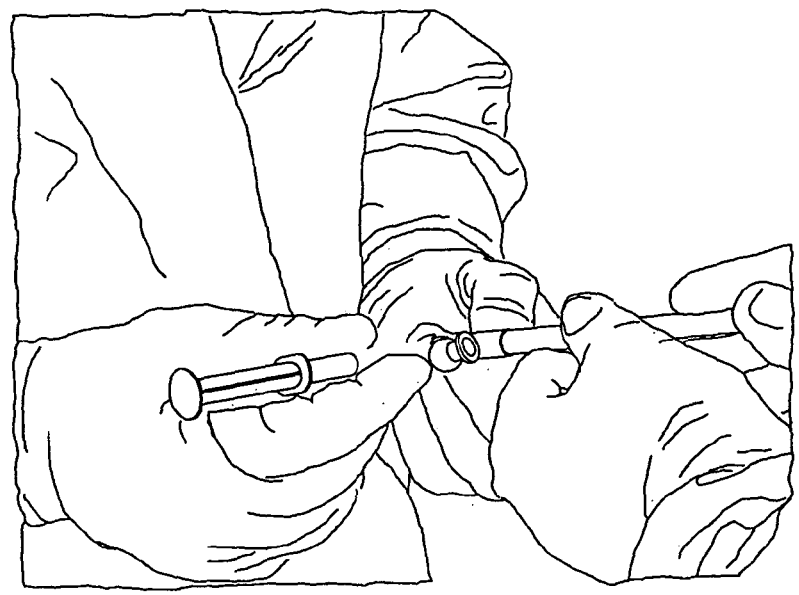
FIG. 11 is a pictorial view of the injection of the cross-linker into the biomaterial mixing system.

Immediately prior to injection, suction is applied to the cavity formed by the removal of tissue during the nucleotomy. A surgical swab may also be used to wick away excess moisture from the injection site. This will ensure that excess fluid does not interfere with the injection of the IDN material. Once the injection site has been prepared, the surgeon will hold the syringe assembly 10 with the crosslinker injection port 12 oriented upward. The entire volume of polymer should now reside in one syringe 14. The sterile assistant will inject the pre-measured volume of crosslinker from the crosslinker syringe 14 into the mixing assembly 10 through the port 12, as shown in FIG. 11.

Figure 12:
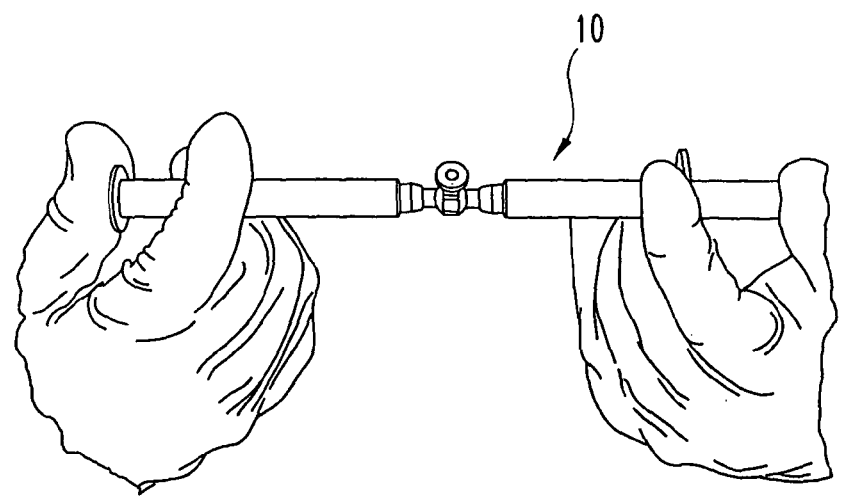
FIG. 12 is a pictorial view of the step of mixing the biomaterial within the mixing system.

The surgeon then mixes the crosslinker and polymer by cycling the plungers of the syringes 14 and 16 back and forth a predetermined number of cycles that is based upon the properties of the particular polymer. For the proteinaceous polymers disclosed in the Protein Polymer patents described above, the plungers are preferably cycled through ten full cycles in ten seconds (FIG. 12). For these polymers, it is important to complete the mixing procedure in ten seconds or less in order to ensure complete and proper mixing of the IDN. Upon completion of the mixing step, the surgeon disassembles the syringe 14 (no insert in the syringe) from the adapter 13. From this point, the surgeon has a fixed amount of working time to perform the injection using the second syringe 16. With the specific polymers, this working time is about 80 seconds. An appropriate previously selected injection needle is connected to the tip of the syringe 16 and the needle is primed with the fully mixed biomaterial composition prior to introducing the needle to the injection site. The initial drops from the injection needle can be ejected onto the surgical field and used as a qualitative gage of the working time of the IDN during the injection procedure.

Figure 13:
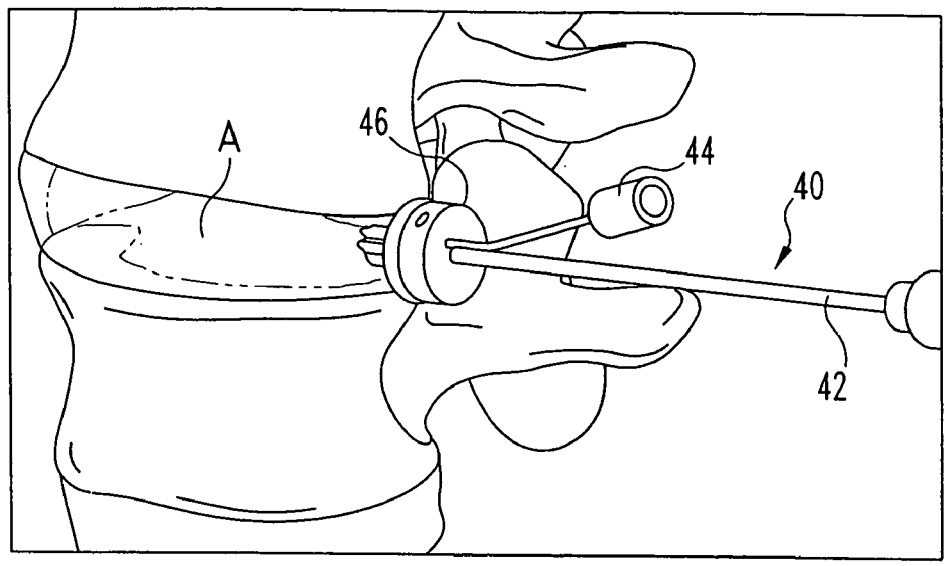
FIG. 13 is a pictorial representation of a vented injection needle assembly in accordance with one aspect of the present invention.

In accordance with one aspect of the invention, the injection needle is provided as part of an injection assembly 40, as shown in FIG. 13. The injection needle 42 extends through a seal element 46 that is configured to provide an essentially fluid tight seal against the disc annulus A. A vent 44 also extends through the seal 46. The seal 46 is shown in more detail in FIG. 15. In the preferred embodiment of the invention, the seal 46 includes a body 48 that is preferably formed of a resilient material that can be compressed slightly under manual pressure. The body 48 defines a sealing face 50 that bears against the disc annulus A (FIG. 13) to form the fluid tight seal.

Figure 15:
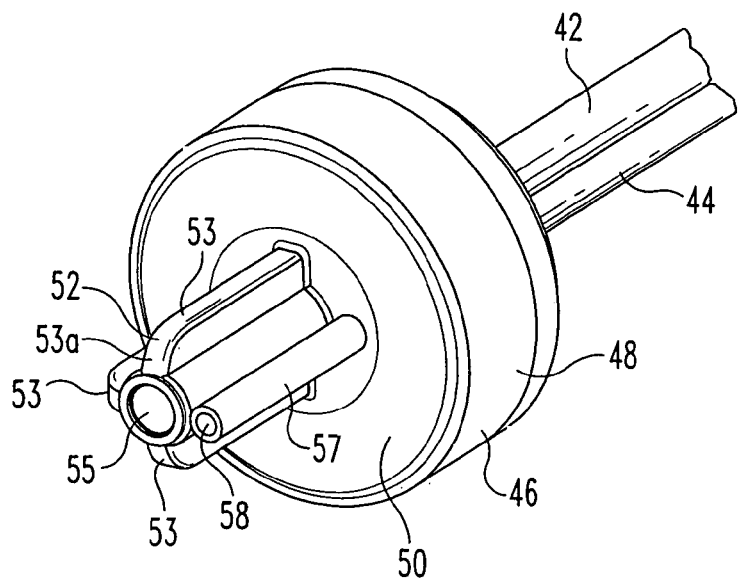
FIG. 15 is a front perspective enlarged view of the vented injection needle in accordance with one embodiment of the invention.

Extending from the sealing face 50 is an engagement boss 52. The boss 52 is preferably configured in accordance with the shape of the annulotomy cut into the annulus. In the illustrated and most preferred embodiment, the annulotomy is cruciate, so that boss 52 is also cruciate in shape. In particular, the boss 52 includes wings 53 that are sized to fit within corresponding legs of the cruciate cut into the annulus A. The leading edges 53a of the wings 53 can be rounded, as shown in FIG. 15, to facilitate placement of the boss 52 within the annulotomy.

The vent 44 provides an additional wing 57 for the boss 52. The wing 57 includes a channel 58 that integrates with the hollow vent 44. Preferably, the vent wing 57 is co-extensive with the other wings 52. Alternatively, the working end of the wing 57 can project slightly farther into the disc space. The injection needle 42 feeds to a channel 55 defined in the boss 52 to provide a pathway for the IDN into the disc cavity.

Figure 14:
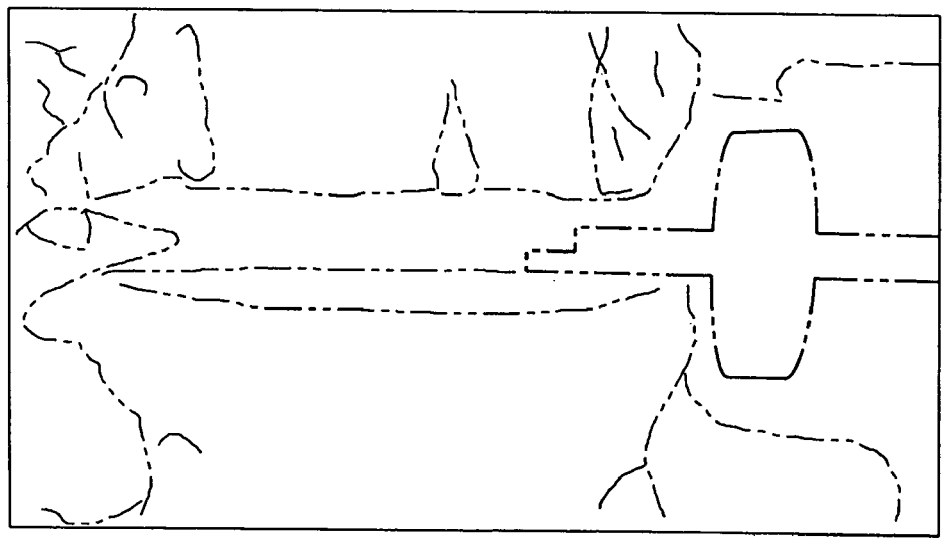
FIG. 14 is a fluoroscopic view of the vented injection needle assembly of FIG. 13 shown in situ.
Figure 16:
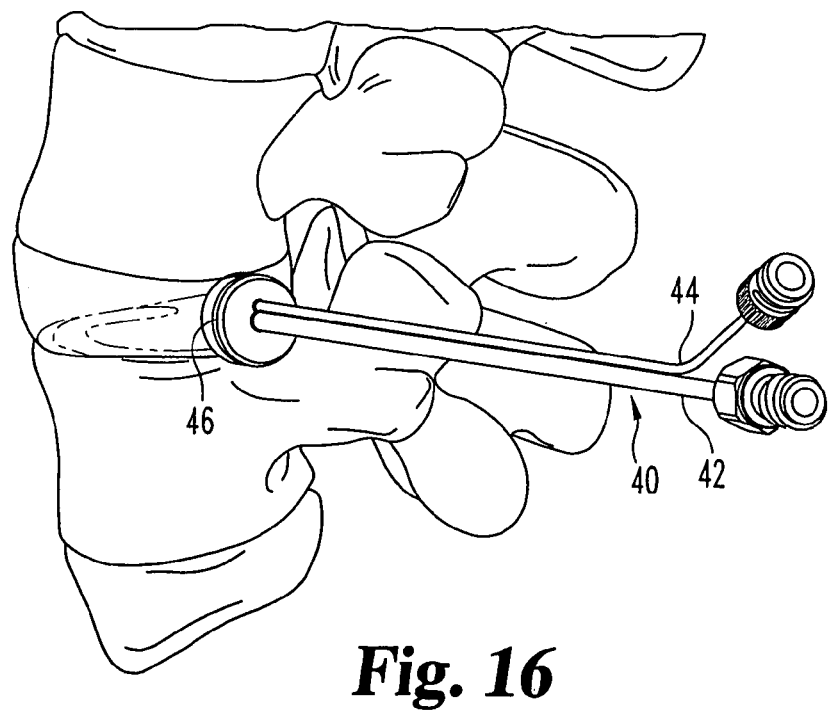
FIG. 16 is an enlarged pictorial view of the vented injection needle depicted in FIG. 15 shown in situ.

In accordance with the preferred method of the invention, the needle is introduced through the annulotomy, while carefully retracting the nerve root, until the plug seal 50 seats against the annulus, as depicted in FIGS. 13-14. Preferably, the needle is positioned so that the vent 44 is facing upward during the injection, as depicted in FIG. 16. Pressure is applied to the seal 46 to ensure no IDN leaks out between the seal and annulus. Preferably, this pressure is applied manually by the surgeon by simply pressing the needle catheter 42 toward the annulus. Since the IDN injection occurs at low pressures, the amount of force required to maintain a fluid-tight seal between the seal face 50 and the annulus is minimal.

Alternatively, the injection assembly 40 may be modified to incorporate various of the sealing techniques described in co-pending application Ser. No. 10/282,755, filed on Oct. 29, 2002 in the name of inventors Boyd et al., and assigned to the assignee of the present invention and application. This co-pending application, entitled "Devices and Methods for the Restoration of a Spinal Disc", was published on May 1, 2003, as Pub. No. US2003/0083641A1. The disclosure of this co-pending application and publication is incorporated herein by reference for all purposes, and specifically the disclosure of the sealing and venting techniques illustrated in FIGS. 11-14 thereof.

The IDN is injected into the space until IDN is seen flowing into or out of the vent tube. In a specific embodiment, the vent tube 44 is clear so that the presence of IDN fluid within the vent can be immediately detected. At this point, the injection is stopped and the needle is held in place until the IDN takes its initial set. A microscope or loupe may be used to visualize the injection process.

In accordance with the preferred embodiment of the invention, the IDN must be allowed to substantially completely cure before the injection needle assembly 40 is removed and the surgical site is closed. The cure period depends upon the particular IDN material. For the specific proteinaceous polymer discussed above, the cure period is a minimum of about five minutes. If IDN material is left within the annulotomy or external to the disc, it is preferably removed using rongeurs after the material has taken its initial set. Suction may also be used around the periphery of the annulotomy to remove cured material.

The volume of IDN injected into the site is preferably recorded from the graduations on the syringe 16. The injection volume will be the difference between the pre- and post-injection graduation readings. The wound is closed and dressed using the surgeon's preferred technique.

As explained above, the IDN is injected under low pressure, which at a minimum means enough pressure so that the IDN will fill all the space left by the excised disc material. The pressure should be sufficient so that the intradiscal cavity can be filled in an acceptable amount of time, which is determined primarily by the cure rate for the IDN. In the illustrated embodiment, the working time for the IDN (i.e., the time from complete mixing of the constituents until the IDN has cured or hardened too much to flow) is about 80 seconds. Thus, the pressure exerted through the syringe should be sufficient to completely fill the intradiscal cavity in about on minute. Manual operation of the syringe is preferred, but it is contemplated that other forms of pressurized injection of the IDN into the disc space is contemplated.

In one important aspect of the invention, the disc space is maintained in its distracted position without the use of external distractors that would otherwise interfere with the injection of the IDN into the space. In other words, using typical physical distraction techniques, the distractor itself will necessarily occupy a certain amount of space within the disc cavity, as well as in the annulotomy. This space must be eventually filled. Moreover, the additional component creates a leak path for the IDN. The present invention avoids these problems altogether.

The seal 46 is formed of a resilient and deformable material so that it can be compressed against the annulus A to form a fluid tight seal. In a preferred embodiment of the invention, the seal 40 is formed of SILASTIC® or a similar elastomeric material. The seal 46 in the illustrated embodiment is cylindrical with a circular sealing face 50; however, other configurations are contemplated provided they can adequately conform to the outer surface of the disc annulus.

In a further variation, the vent 44 can simply constitute a vent opening in the seal 46. The vent tube 44 is preferred because it carries the vented fluid away from the surgical site and can bring the discharge opening within clear view of the surgeon. As a further alternative, the seal 46 can be separate from the injection needle 42 and vent tube 44. In other words, the channels 55 and 57 can extend through the body 48 of the seal 46. Catheters for the injection needle and vent can extend into the appropriate channel, preferably with a press-fit or fluid-tight engagement.

Figure 18:
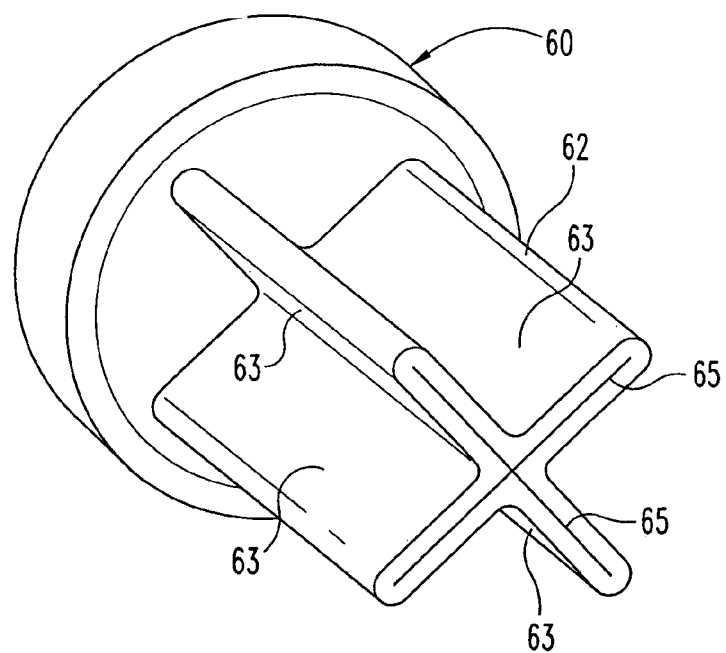
FIG. 18 is an enlarged perspective view of a seal in accordance with a further embodiment of the invention.

In yet another alternative, the cruciform boss 52 can be in the form of a duck-bill valve, as shown in FIG. 18. In particular, the seal 60 includes a valve boss 62 in the form of a cruciform duckbill valve. Each wing 63 of the boss 62 includes a slit passageway 65 that expands under fluid pressure. Thus, as fluid flows into the seal 60, the duckbill valve wings 63 expand to allow the fluid to flow into the disc space. Moreover, this expansion of the valve boss 62 enhances the seal between the cruciate boss and the annulotomy.

In the illustrated embodiment, the system and method of the present invention has been applied to the injection of an IDN into a disc space. The present system and method can be modified to provide low pressure injection of a biomaterial into other sites or cavities, such as within a vertebral body.

The present invention contemplates injection of a biomaterial into a body cavity, such as an excised disc space, under low pressure. A further feature of the invention resides in the provision of a seal against the cavity opening that can be easily maintained against the low pressure injection of the biomaterial. Another feature more specific to injection of an IDN is the method of pre-distraction of the disc space, maintaining the distraction without the use of a separate distraction tool and injecting the biomaterial into the distracted space to completely fill the space.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method of treating a diseased or damaged spinal disc having an inner nucleus pulposus and an outer annulus, comprising the steps of:
   providing access to the nucleus pulposus through the annulus;
   removing at least a portion of said nucleus pulposus to create an intradiscal space;
   determining the size of said intradiscal space by substantially filling said intradiscal space with a fluid solution, removing said solution and measuring the volume of the removed solution; and then
   sealably introducing under pressure a quantity of a curable biomaterial, different from said fluid solution, through said annulus directly into said intradiscal space, said quantity based on said determining step.

2. The method of claim 1, wherein said access is provided by an extraforaminal approach to the disc.

3. The method of claim 2, wherein said extraforaminal approach is selected from the group of surgical entries consisting of a lateral retroperitoneal approach and a paramedian approach through the paraspinal muscles.

4. The method of claim 1, wherein said access is an opening extending through the annulus.

5. The method of claim 4, wherein the opening is formed by an annulotomy.

6. The method of claim 5, wherein an annulotomy creating a cruciate form is performed.

7. The method of claim 4, wherein said step of determining the size of said intradiscal space is practiced by expanding an inflatable device within said intradiscal space with said fluid solution.

8. The method of claim 7, wherein said inflatable device is a compliant balloon inserted into said intradiscal space in a deflated condition and inflated within said intradiscal space until it stops against the far border of said intradiscal space.

9. The method of claim 7, wherein said inflatable device is a compliant balloon substantially filled with said fluid solution, and wherein said fluid solution contains a contrast medium capable of visualization under fluoroscopy.

10. The method of claim 9, further including the step of determining the location of said compliant balloon in said intradiscal space.

11. The method of claim 4, wherein said curable material is sealably introduced through a needle inserted through said opening.

12. The method of claim 11, further including the step of providing a vent in communication with said intradiscal space.

13. The method of claim 12, wherein said needle and said vent are inserted through said opening.

14. The method of claim 12, wherein said material is introduced until a quantity of said material flows into said vent.

15. The method of claim 11, further including the step of providing a seal for sealing said annulus opening.

16. The method of claim 15, wherein said seal is provided on said needle.

17. The method of claim 16, wherein said seal comprises a compressible portion, said method comprising the further step of placing said compressible portion against the exterior surface of said annulus adjacent to said opening.

18. The method of claim 17, wherein said seal is configured to have a boss portion projecting from said compressible portion and configured to reside in the opening of said annulus.

19. The method of claim 17, wherein said compressible portion is pressed by manual pressure against said exterior surface of said annulus.

20. The method of claim 19, wherein said compressible portion is held against said exterior surface for a period of time to allow at least a partial curing of said biomaterial.

21. The method of claim 20, wherein said period of time is up to about five (5) minutes.

22. The method of claim 11, wherein said curable biomaterial is injected into said intradiscal space through said needle under relatively low pressure.

23. The method of claim 22, wherein said injection pressure is less than about 100 psi.

24. The method of claim 23, wherein said pressure is within the range of about 25 to 40 psi.

25. The method of claim 22, wherein said pressure is applied manually with a syringe.

26. The method of claim 22, wherein said pressure is maintained for a period of time until said biomaterial is at least partially cured.

27. The method of claim 26, wherein said period of time is up to about five (5) minutes.

28. The method of claim 1, wherein said intradiscal space communicates with opposing, spaced vertebral bodies, and wherein said method further includes the step of applying a force to distract said opposing vertebral bodies about the intradiscal space.

29. The method of claim 28, wherein said distraction force is removed prior to the step of introducing said biomaterial into said intradiscal space.

30. The method of claim 28, wherein said distraction force is applied by inserting an inflatable device through said opening in a deflated condition and inflating said inflatable device within said intradiscal space.

31. The method of claim 30, wherein said inflatable device is a non-compliant balloon.

32. The method of claim 31, wherein said non-compliant balloon is configured to provide a limit to lateral expansion upon inflation but to allow further expansion in the direction of the opposing vertebral bodies.

33. The method of claim 31, wherein said distraction force is held for a period of time sufficient to allow the distracted vertebral bodies to remain substantially distracted by natural stretching of ligaments surrounding said vertebral bodies.

34. The method of claim 33, wherein said distraction force is applied by inflating said balloon to a first pressure and held at said pressure for said period of time.

35. The method of claim 34, wherein said first pressure is up to about 200 psi.

36. The method of claim 34, wherein said period of time is not less than about 20-30 seconds.

37. The method of claim 34, wherein said step of removing said distraction force includes releasing the first pressure after said period of time.

38. The method of claim 37, further including the step of removing the balloon from the intradiscal space.

39. The method of claim 38, wherein said biomaterial is sealably introduced into said intradiscal space by injection through a needle inserted through said opening.

40. The method of claim 39, wherein said biomaterial is injected into said intradiscal space at a second pressure lower than said first pressure.

41. The method of claim 40 wherein said pressure is less than about 100 psi.

42. The method of claim 41, wherein said pressure is within the range of about 25-40 psi.

43. The method of claim 39, further including the step of providing a vent in communication with said intradiscal space to exhaust said intradiscal space and allow biomaterial to seep out when the intradiscal space is substantially filled.

44. The method of claim 1, wherein said fluid solution contains an additive selected from the group consisting of saline and contrast media.

45. The method of claim 1, wherein the step of determining the size is practiced by including a contrast medium in said fluid solution and visualizing the size of the intradiscal space under fluoroscopy before removing said fluid solution.

46. A method of treating a diseased or damaged spinal disc having an inner nucleus pulposus and an outer annulus, comprising the steps of:
   forming an opening through said annulus to provide access to the nucleus pulposus;
   removing at least a portion of the nucleus pulposus to create an intradiscal space;
   determining the size of said intradiscal space with a fluid solution including a contrast medium; then
   introducing into said annulus opening a vented needle with a seal in a manner such that said seal forms a fluid-tight seal about said opening and said vented needle communicates with said intradiscal space; and
   introducing under pressure a quantity of a curable biomaterial through said needle directly into said intradiscal space, said quantity based on said determining step.

47. The method of claim 46, wherein said seal is provided on said needle.

48. The method of claim 47, wherein said seal is configured to have a compressible face portion of extent greater than the size of said opening, said face portion placed against the exterior surface of said annulus adjacent said opening while said vented needle communicates with said intradiscal space.

49. The method of claim 48, wherein said seal is configured to have a boss portion projecting from said compressible face portion and configured to reside in the opening of said annulus.

50. The method of claim 49, wherein said vented needle comprises independent channels respectively defining a needle channel for the injection of biomaterial and a vent channel for exhausting said intradiscal space.

51. The method of claim 50, wherein said needle channel and said vent channel extend through said seal.

52. The method of claim 49, wherein said boss portion is configured to have a complementary shape of said opening in said annulus.

53. The method of claim 52, wherein said opening in said annulus and said boss portion are cruciate in shape.

54. The method of claim 49, wherein said boss portion comprises a duck-bill valve having a slit passageway extending through said boss portion and configured to allow expansion of said boss portion upon passage of biomaterial therethrough under pressure.

55. The method of claim 54, wherein said boss portion is configured in a cruciate shape formed by four wing portions, each wing portion having a respective duck-bill valve defined by a slit passageway extending therethrough.

56. The method of claim 46, wherein the step of determining the size is practiced by substantially filling said intradiscal space with said fluid solution, removing said fluid solution and estimating the volume of fluid solution removed from said intradiscal space.

57. A method of treating a diseased or damaged spinal disc between two opposing vertebral bodies having an inner nucleus pulposus and an outer annulus, comprising the steps of:
  performing an annulotomy to create an opening through said annulus;
  performing a nucleotomy to remove at least a portion of said nucleus pulposus and create and intradiscal space;
  distracting the opposed vertebral bodies about the intradiscal space;
  determining the size of the created intradiscal space;
  providing a vented needle with a seal thereon;
  inserting said vented needle into said opening through said annulus and in communication with said intradiscal space and placing said seal against at least the exterior surface of said annulus adjacent said opening to form a fluid-tight seal thereat;
  introducing under an introduction pressure a quantity of a curable biomaterial through said needle directly into said intradiscal space, said quantity based on said determining step; and
  substantially maintaining said introduction pressure and said seal until said biomaterial is at least partially cured.

58. The method of claim 57, wherein the step of distracting the opposed vertebral bodies is effected by inserting an inflatable balloon through said opening in said annulus in a deflated condition and inflating said balloon at an inflation pressure to cause said opposing vertebral bodies to further separate relative to each other.

59. The method of claim 58, further including the step of releasing the inflation pressure and deflating said balloon subsequent to distracting said opposing vertebral bodies and removing said balloon from said intradiscal space.

60. The method of claim 59, wherein said introduction pressure is selected to substantially maintain the distracted intradiscal space subsequent to the removal of said balloon.

61. The method of claim 60, wherein said introduction pressure at which said biomaterial is introduced into said intradiscal space is less than said inflation pressure at which said balloon is inflated to distract said opposing vertebral bodies.

62. The method of claim 58, wherein said inflatable balloon is non-compliant.

63. The method of claim 57, wherein said step of determining the size of said intradiscal space is practiced by expanding a compliant balloon within said intradiscal space.

64. The method of claim 63, wherein the step of determining the size is practiced by measuring the expanded balloon while in said intradiscal space.

65. The method of claim 57, wherein said vented needle comprises independent channels respectively defining a needle channel for introduction of said biomaterial and a vent channel for exhausting said intradiscal space.

66. The method of claim 65, wherein said biomaterial is introduced until a quantity of such biomaterial seeps into said vent channel.

* * * * *